(12) United States Patent
Görlich et al.

(10) Patent No.: US 6,335,385 B2
(45) Date of Patent: Jan. 1, 2002

(54) METHOD OF MAKING A DENTAL PROSTHESIS AND CURABLE SYSTEM

(75) Inventors: Karl Joachin Görlich, Fürth; Wigbert Hauner, Langen; Ralf Janda, Frankfurt, all of (DE)

(73) Assignee: Dentsply GmbH (DE)

( * ) Notice: Subject to any disclaimer, the term of this patent is extended or adjusted under 35 U.S.C. 154(b) by 0 days.

(21) Appl. No.: 09/798,270

(22) Filed: Mar. 2, 2001

Related U.S. Application Data

(63) Continuation of application No. 08/556,233, filed on Nov. 9, 1995, now abandoned, which is a continuation of application No. 08/243,352, filed on May 16, 1994, now abandoned.

(51) Int. Cl.$^7$ ............................................. A61K 6/083
(52) U.S. Cl. ........................ 523/115; 113/120; 425/2; 425/178; 425/DIG. 11; 264/16; 264/17; 264/19; 264/22; 522/908
(58) Field of Search ........................ 523/113, 115, 523/120; 425/2, DIG. 11, 178; 264/16, 17, 19, 22; 522/908

(56) References Cited

U.S. PATENT DOCUMENTS

| | | | |
|---|---|---|---|
| 68,548 A | 9/1867 | Bean ........................... 425/180 |
| 283,487 A | 8/1883 | House ......................... 425/180 |
| 1,575,688 A | 3/1926 | Joannides ................. 425/129.1 |
| 2,341,991 A | 2/1944 | Jackson ......................... 18/30 |
| 2,660,758 A | 12/1953 | Hennicke ....................... 18/33 |
| 3,635,630 A | 1/1972 | Greene ........................ 425/175 |
| 4,069,000 A | 1/1978 | Hampshire ................... 425/395 |
| 4,182,507 A | 1/1980 | Bekey et al. .................. 249/54 |
| 4,218,205 A | 8/1980 | Beu ............................. 425/180 |
| 4,281,991 A | * 8/1981 | Michl et al. ................ 523/115 |
| 4,328,325 A | 5/1982 | Marquaedt et al. .......... 526/301 |
| 4,359,435 A | 11/1982 | Kogure ....................... 264/40.5 |
| 4,599,216 A | 7/1986 | Rohrer et al. ................. 422/21 |
| 4,873,269 A | * 10/1989 | Nakazato .................... 523/115 |
| 4,971,735 A | 11/1990 | Uebayashi ................... 264/17 |
| 5,047,455 A | 9/1991 | Hesse et al. ................. 523/508 |
| 5,063,255 A | * 11/1991 | Hasegawa et al. .......... 522/908 |
| 5,066,231 A | 11/1991 | Oxman et al. ............... 433/214 |
| 5,094,619 A | 3/1992 | McLaughlin ............. 433/203.1 |
| 5,104,591 A | 4/1992 | Masuhara et al. ............ 264/16 |
| 5,108,753 A | 4/1992 | Kuberasampath et al. .. 424/422 |
| 5,151,279 A | * 9/1992 | Kimura ....................... 425/178 |
| 5,158,717 A | 10/1992 | Lai ............................. 264/1.1 |
| 5,183,834 A | * 2/1993 | Gorlich et al. .............. 523/116 |
| 5,270,357 A | * 12/1993 | Hesse et al. ................. 523/526 |
| 5,324,186 A | * 6/1994 | Bakanowski ................ 425/116 |

FOREIGN PATENT DOCUMENTS

| | | |
|---|---|---|
| DE | 3236835 A1 | 4/1984 |
| DE | 3725502 | 2/1988 |
| DE | 41 02 129 A1 | 7/1992 |
| EP | 0 089 705 | 2/1983 |
| EP | 0 193 514 | 1/1986 |
| JP | 60-214284 | 10/1985 |
| JP | 62-54739 | 3/1987 |

OTHER PUBLICATIONS

Ullmann's Encyclopedia of Industrial Chemistry, vol. A8, Chap. 5.1, 1987, VCH; Verlagsgesellschaft, Weinheim, DE, pp. 278–280, R. Janda: "Denture Based Resins".

Patent Abstract of Japan, vol. 013, No. 124 (C–580), Mar. 27, 1989 and JP A–63 296750 (Shintaro Oshima et al) Dec. 2, 1988 *abstract).

Patent Abstract of Japan vol. 016 No. 329 (c–963), Jul. 17, 1992 and JP–A–04 096746 (Shiken KK et al) 30 *abstract*.

John J. Sharry; Complete denture prosthodontics; third edition; McGraw–Hill, 1974; pp. 268–272.

Heraeus Kulzer: Palamat practice.

* cited by examiner

*Primary Examiner*—Peter Szekely
(74) *Attorney, Agent, or Firm*—Dale R. Lovercheck; James B. Bieber

(57) ABSTRACT

The invention provides a curable system and method of making a dental prosthesis. The method of making a dental prosthesis includes providing a one component denture base resin composition which is polymerizable by microwave energy. The one component denture base resin composition is injected into a mold enclosed by a flask having a body wall which is substantially transparent to the microwave energy. The curable system includes microwave energy sensitive initiators and polymerizables (meth)acrylate Monomers having molecular weights preferably between 400 and 20,000. The initiators are adapted to initiate polymerization of the polymerizable Monomers by application of microwave energy to the flask. The initiators are adapted to remain stable and not initiate polymerization of the Monomers for at least one year at 23° C. in the absence of microwave energy.

37 Claims, 6 Drawing Sheets

METHOD OF MAKING A DENTAL PROSTHESIS AND CURABLE SYSTEM

This application is a continuation of application Ser. No. 08/556,233, filed Nov. 9, 1995, abandoned, which is a continuation of application Ser. No. 08/243,352 filed May 16, 1994, abandoned.

The invention relates to methods of making dental prostheses from microwave curable dental compositions. The invention provides a method of making a dental prosthesis in which a pasty one component denture base resin polymerizable by microwave energy is injected into a mold enclosed by a flask. The flask has a body wall, at least a substantial portion of which is effectively transparent to the microwave energy. Useful in carrying out the method of the invention is a system which includes dental compositions containing Monomer(s) and an initiator system for initiation of polymerization of the Monomer(s) by application of microwave energy to form dental products having low shrinkage, high flexural strength and high modulus of elasticity. Dentures thus formed have a close fit to the patient's mouth due to the low shrinkage of the pasty composition.

Prior art denture bases have been manufactured using powders based on polymethyl methacrylate and liquids based on methyl methacrylate, as see R. Janda, Ullmann's Encyclopedia of Industrial Chemistry, Vol. A 8, Chap. 5.1 Denture Base Resins, p. 278/280, 1987 Editor VCH Verlagsgesellschaft Weinheim, Germany. These powder and liquid materials require mixing to form a dough. More than ten minutes after mixing the powder and liquid are required before the dough is moldable. The liquids contain more than 90% by weight methyl methacrylate which has a strong odor during processing, and the polymerized denture base material formed has an allergenic potential because of residual unpolymerized monomer.

Bean in U.S. Pat. No. 68,548 discloses improved apparatus for and method of casting aluminum. Housel in U.S. Pat. No. 283,487 discloses dentist's flask. Joannides in U.S. Pat. No. 1,575,688 discloses manufacture of dental plates and apparatus therefore. Jackson in U.S. Pat. No. 2,341,991 discloses injecting mechanism for dental flasks. Hennicke et al in U.S. Pat. No. 2,660,758 discloses injection flask apparatus. Greene in U.S. Pat. No. 3,635,630 discloses denture molding apparatus including flask members with removable plastic inserts. Rohrer et al in U.S. Pat. No. 4,599,216 discloses apparatus for exposure to microwaves. Hampshire in U.S. Pat. No. 4,069,000 discloses mold for shaping and curing reinforced plastic material. Bekey et al in U.S. Pat. No. 4,182,507 discloses mold for casting articulated castings from registered dental impressions. Beu in U.S. Pat. No. 4,218,205 disclose three-section self-sealing dental flask. Kogure in U.S. Pat. No. 4,359,435 discloses method for manufacturing plastic products. Nakazato in U.S. Pat. No. 4,873,269 discloses resinous compositions for denture base. Uebayashi in U.S. Pat. No. 4,971,735 discloses fabricating method of resin base denture. Hasegawa et al in U.S. Pat. No. 5,063,255 discloses photopolymerizable type resin compositions for dental purposes. Oxman et al in U.S. Pat. No. 5,066,231 discloses dental impression process using polycaprolactone molding composition. McLaughlin in U.S. Pat. No. 5,094,619 discloses coloration of dental restorations. Masuhara et al in U.S. Pat. No. 5,104,591 discloses method for light curing of dental light-curing resins. Kuberasampath et al in U.S. Pat. No. 5,108,753 discloses osteogenic devices. Kimura in U.S. Pat. No. 5,151,279 discloses method for making resin dental plates and flasks. Lai in U.S. Pat. No. 5,158,717 discloses method of molding shaped polymeric articles. Fujii et al in Japanese Patent 62-54739 discloses vulcanization accelerator. Nakayama et al in Japanese Patent 60-214284 discloses pulse radar. Frisch in Offenlegungsschrift Patent DE 32 36 835 A1 discloses resin preparation for tooth prosthesis. Nakazato in Offenlegungsschrift DE 41 02 129 A1 discloses a method and device for products to repair from dental prosthesis synthetic material. Feurere et al in European Patent 0 089 705 B1 discloses procedure for the fabrication by molding. De Clerck in European Patent No. 0 193 514 B1 discloses procedure of polymerizing resins.

It is an object of the present invention to provide a method for making precisely fitting prosthesis, especially crowns, bridges, full or partial dentures using microwave energy to initiate polymerization.

It is an object of the present invention to provide a system containing a one component polymeric composition for producing dental prosthesis which is readily cured by using microwave energy and which has a polymerization shrinkage of less than 4% by volume.

It is an object of the present invention to provide a system containing a one component composition which is methyl methacrylate free.

It is an object of the present invention to provide a system containing a curable composition, including polymerizable acrylate and/or methacrylate Monomers having molecular weight between 120 and 50,000 and initiators adapted to remain stable and not initiate polymerization of the polymerizable Monomers when stored for more than one year at 23° C.

It is an object of the present invention to provide a method of making a denture by injecting a one component composition into a mold within a closed flask.

It is an object of the present invention to provide a method of making a dental prosthesis by curing the injected one component denture base resin within a mold contained by a closed flask by applying microwave energy.

It is an object of the present invention to provide a method of making a dental prosthesis by providing a one component polymerizable composition and injecting the said composition into an enclosure having a body wall which is substantially transparent to microwave energy.

It is an object of the present invention to provide a curable system, including a microwave permeable flask enclosing a polymerizable composition having at least one polymerizable methacrylate or acrylate Monomer with a molecular weight between 120 and 50,000, preferably 120 to 20,000 g/mol, and fillers and a microwave energy sensitive initiator system adapted to permit the polymerizable compound to remain substantially and effectively free of polymerization, and moldable for at least one year when stored at 23° C.

As used herein "microwave transparent" refers to materials through which microwaves are transmitted without being substantially absorbed.

As used herein "denture" refers to a molded member formed with at least one artificial teeth embedded therein.

As used herein "Monomers" refers to monomers and/or oligomers.

Throughout this disclosure all percentages are percent by weight unless otherwise indicated.

BRIEF DESCRIPTION OF THE INVENTION

The invention provides a curable system and method of making a dental prosthesis. The method of making a dental prosthesis includes providing a one component denture base resin composition which is polymerizable by microwave energy. The one component denture base resin composition is injected into a mold enclosed by a flask having a body wall which is substantially transparent to the microwave energy. The curable system includes microwave energy sensitive initiators and polymerizable (meth)acrylate Monomers having a molecular weight preferably between 120 and 20,000. The initiators are adapted to initiate polyermization of the polymerizable Monomers by application of microwave energy to the flask. The initiators are adapted to remain stable and not initiate polymerization of the Monomers for at least one year at 23° C. in the absence of microwave energy.

DETAILED DESCRIPTION OF THE INVENTION

A precisely fitting denture is made in accordance with the invention by injecting a shelf stable polymerizable one component denture base resin composition into a mold within a closed flask and then applying microwave energy to the flask to initiate polymerization of the polymerizable composition. The one component denture base resin composition includes one or more acrylate and/or methacrylate Monomers having molecular weights between 120 and 50,000 g/mol, fillers and an initiator system. Most preferably the Monomers have a molecular weight from 120 to 20,000 g/mol. Preferred fillers are inorganic and/or organic particles and/or fibers. Preferably the polymerizable composition includes accelerators, stabilizers and pigments. Polymerization of the Monomers is initiated by the initiators upon activation by microwave energy. The initiators remains stable in the absence of microwave energy for at least one year at 23° C. The polymerizable one component denture base resin composition shrinks less than 4% during the polymerization process.

The invention is now described with more particular reference to FIGS. 1 to 6. With more particular reference to FIGS. 1, 1A and 1B it is seen that flask 1 includes upper flask half 1B, and lower flask half 1A and a space retainer 2. Each flask half 1A and 1B is made of fiber reinforced polymeric material which is microwave transparent and adapted to be exposed to a microwave field. In closed positions lower and upper flask halves 1A and 1B are connected by connectors, such as screws or bolts which extend through apertures (borings) 3 and 3A. The connectors are adjusted to hold the halves 1A and 1B of flask 1 tightly together. Microwave transparent resin flask 1 is made for example of polyester, polyethylene, polypropylene, polysulfone, polyethersulphone, polyoxymethylene, and/or polyetherether ketone. The aforesaid mentioned plastic materials may be reinforced with fibres such as glass fibres or organic fibres as for example, polyamides-, polyimide-fibres. The polymerizable composition is a mixture of high molecular weight mono-, di-, or multifunctional polymerizable methacrylates and/or acrylates, inorganic and/or organic fillers and initiators for radical polymerization. The polymerizable composition optionally includes pigments, stabilizers, plasticizers and other additives.

Figure 1:
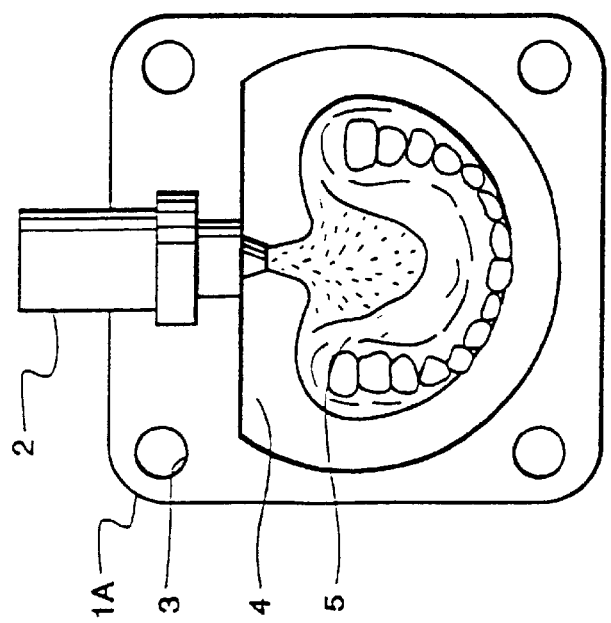
FIG. 1 is a top view of the lower flask half shown in FIG. 1A with an upper denture and made in wax, with the artificial teeth set up and with the injection channel(s) made in wax leading to the space retainer for use in accordance with the invention.
Figure 1A:
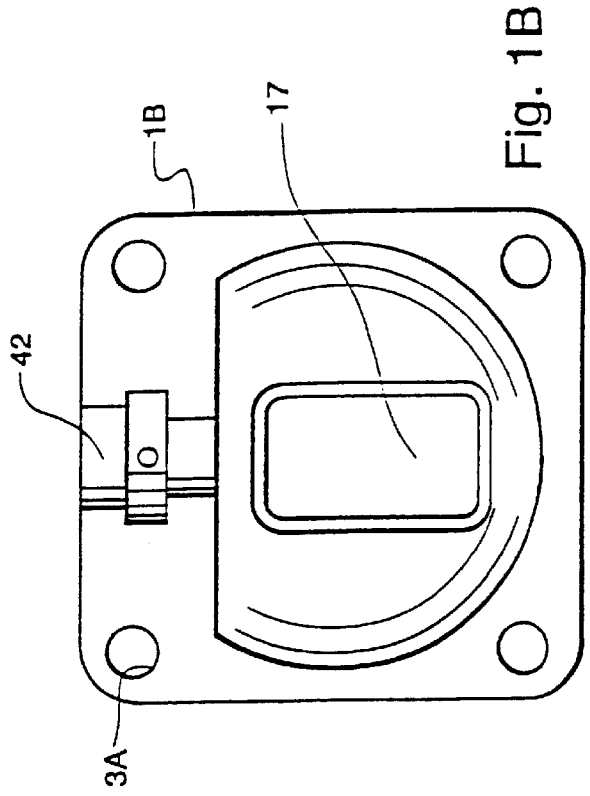
FIG. 1A is a perspective view of a flask in accordance with the invention.
Figure 1B:
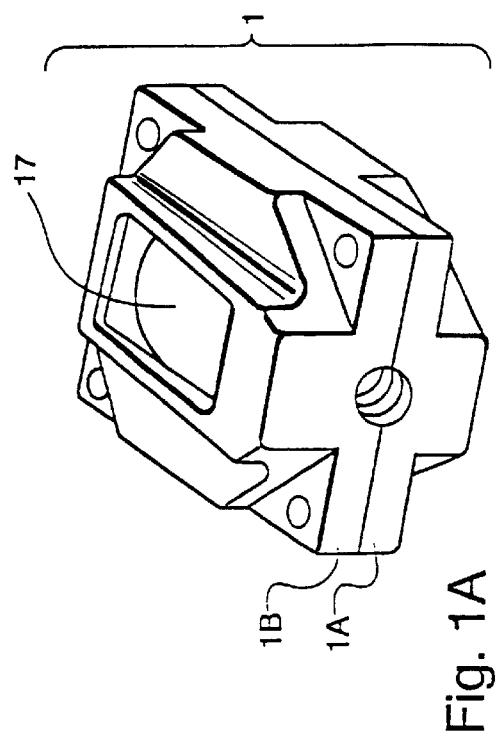
FIG. 1B is a top view of the upper half of the flask shown in FIG. 1A.
Figure 3:
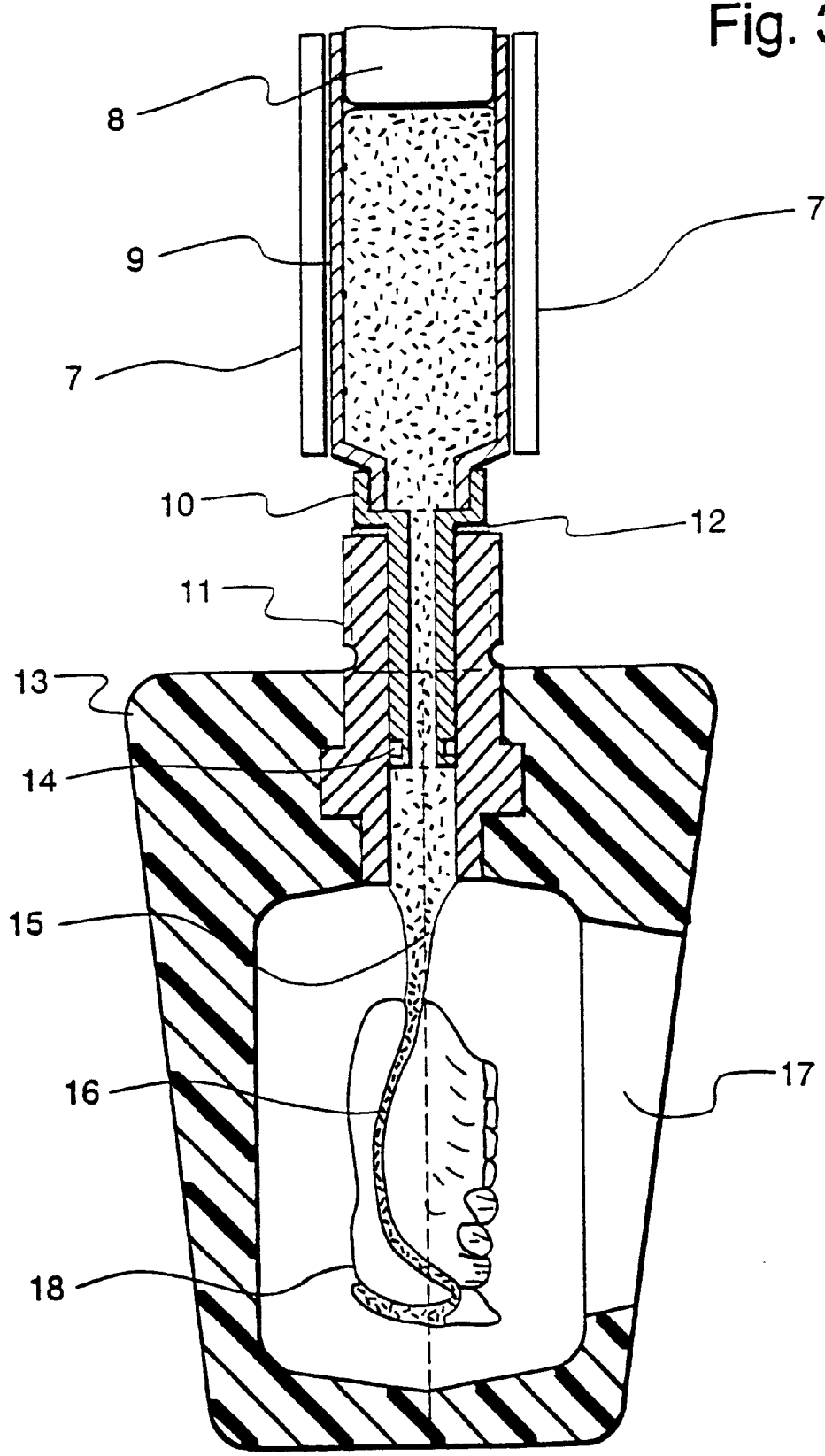
FIG. 3 is a cross-sectional view of a flask with teeth embedded, and one component denture base resin being injected for use in accordance with the invention.
Figure 6:
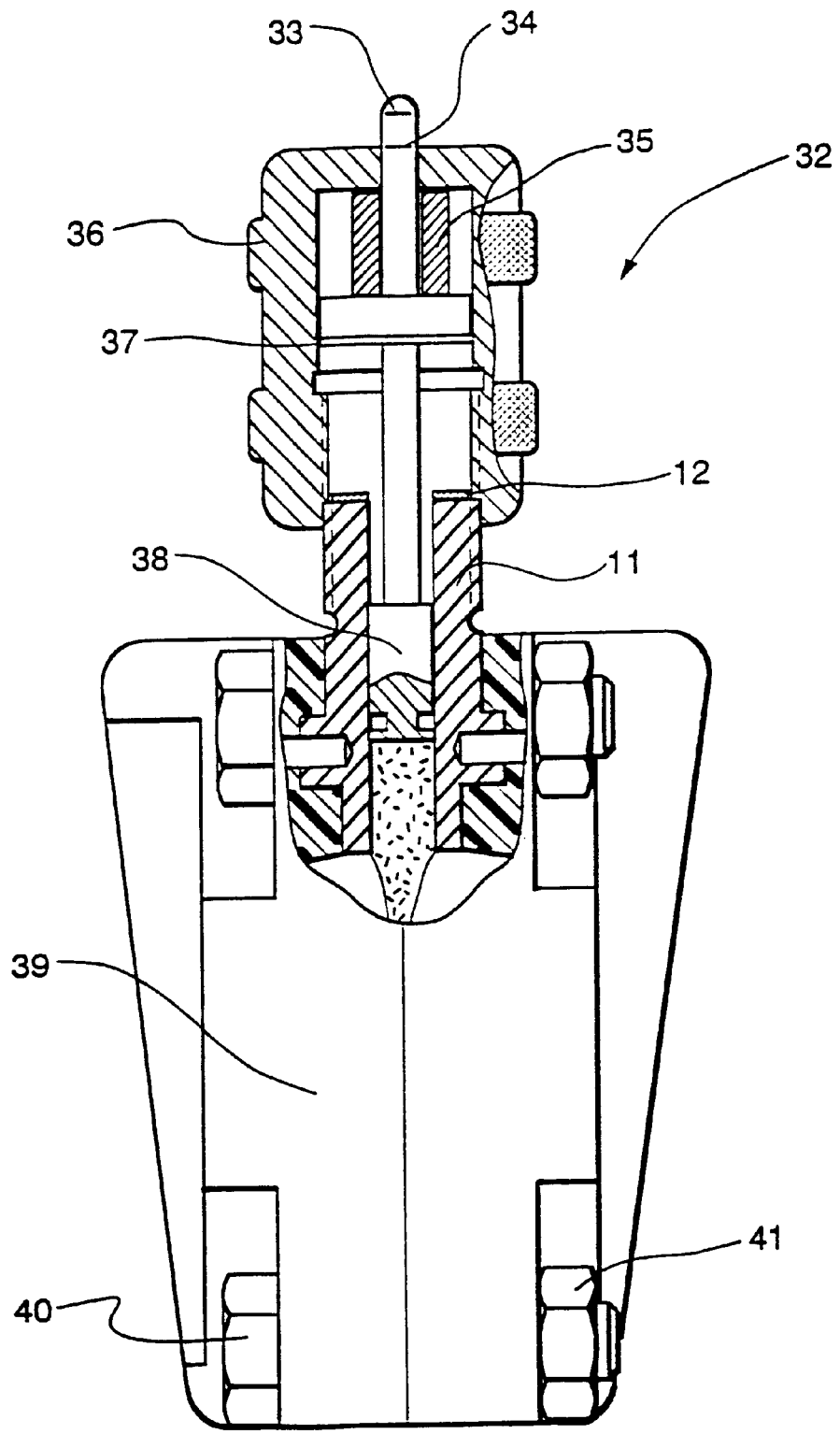
FIG. 6 is a cross-sectional view of a flask and a repressing device fixed on the injection opening of the flask for use in accordance with the invention.

A denture in accordance with a preferred embodiment of the invention is made from an impression of a patient's mouth formed in a conventional impression material as a negative model. A solid plaster model or positive model of the impression of the patients mouth is prepared in a conventional manner. Next, a denture is shaped in wax on the plaster model and the artificial teeth are set up according to the gnathological rules. A space retainer 2 having the same shape as the metal banjo bolt 11 as shown in FIG. 3, is inserted in the prefabricated opening 42, of the lower flask half 1A, as shown in FIG. 1. Then flask half 1A is filled with plaster and the solid plaster model carrying the waxed up denture is half embedded into the fluid plaster. Next, an injection channel is modeled in wax to upper denture 5. Two injection channels are modeled in wax to lower denture 6. The set plaster is isolated with a separating solution (such as Isolant, sold by Dentsply International Inc.). Upper flask half 1B is then positioned on lower flask half 1A and fixed with fibre reinforced resin bolts 40 and nuts 41 as shown in FIG. 6. Then plaster is poured through a hole 17 in the upper flask half 1B into the closed flask in order to completely embed the wax-up of the denture and the injection channels.

After the plaster has set completely, flask halves 1A and 1B are separated and the wax is later removed with hot water.

Figure 2:
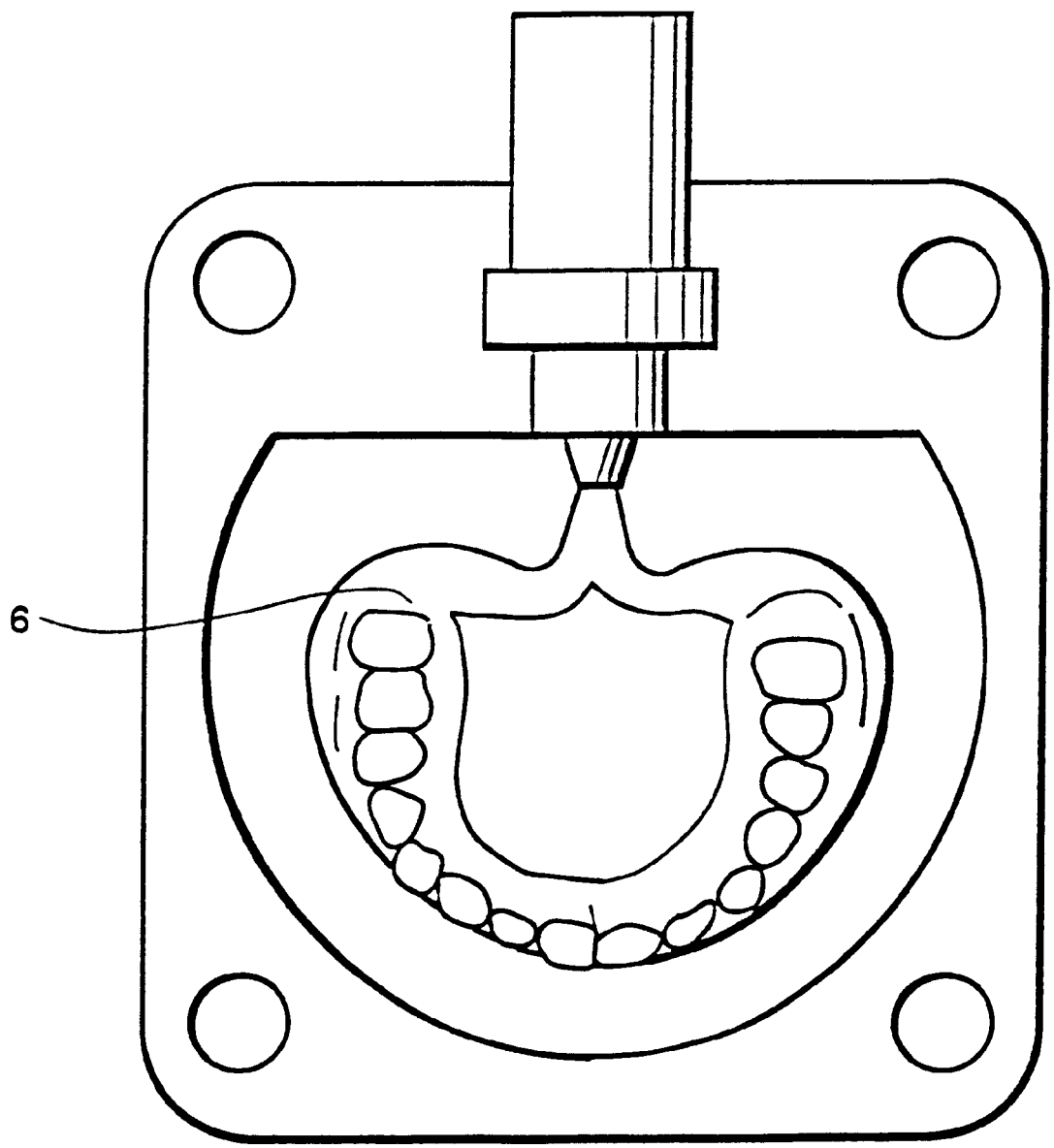
FIG. 2 is a top view of a lower flask half with a lower denture.

Channel wall 17 is provided in the upper flask half 1B of the flask 1 to provide a passage through which to fill the closed flask 1 with plaster to form mold 4. Plaster mold 4 is enclosed by closed flask 1. In mold 4 is embedded a model of upper denture 5 which is made of wax with a set of artificial teeth inserted therein. An injection channel made of wax, leads to the space retainer 2 from the model of upper denture 5 in lower flask half 1A. A model of lower denture 6 made in wax, with the artificial teeth set therein and with two injection channels, made of wax leading to a space retainer is shown in FIG. 2. A denture mold is formed by heating and draining the wax from the plaster mold.

The mating plaster areas and the walls of the cavity are coated with known alginate separating solutions and the basal (base) sides of the teeth are prepared by known techniques. The space retainer 2 is removed and the metal banjo bolt 11 is inserted. The metal banjo bolt 11 supports the injection cartridge and protects the one component denture base resin being injected against the microwaves so that a microwave impermeable conduit is formed allowing the one component denture base resin situated inside the metal banjo bolt 11 to remain unpolymerized during subsequent polymerization of the resin to form a denture so that the hardened denture may be separated from said conduit. Resin shell 12, mouth piece 10, and injection cartridge 9 and metal banjo bolt 11 are positioned on top of flask 1 which is then placed into injection device 19. Injection device 19 is then closed.

FIG. 3, shows a cartridge 9 supported by and within a cartridge shell 7. Cartridge 9 contains one component denture base resin composition 15 to which pressure is applied by means of cartridge press stamp 8. Pressure applied by cartridge press stamp 8 moves it downwardly within and into transparent resin injection cartridge 9. Cartridge press stamp 8 forces one component denture base resin composition 15 through mouth piece 10 and into mold Chamber 18 within mold 4. Mouth piece 10 is supported by metal banjo bolt 11 and resin shell 12 which extend into fibre reinforced microwave transparent resin flask 13. Safety ring 14 is supported within a groove at the lower end of mouth piece 10. One component denture base resin composition 15 forms denture base 16 after being injected into mold chamber 18 of mold 4 enclosed by flask 1.

Figure 4:
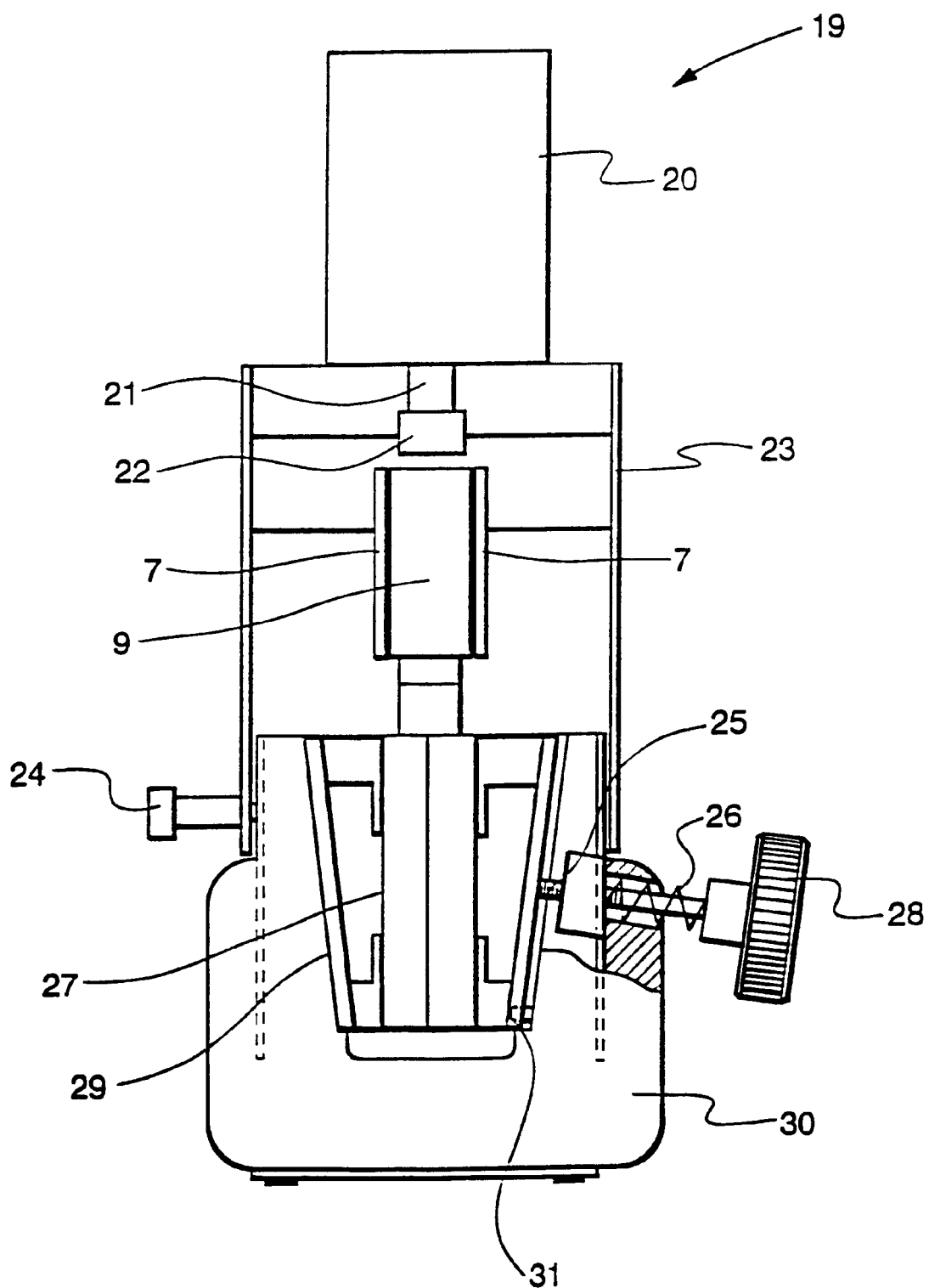
FIG. 4 is a frontal view of an injection device with a flask inserted for use in accordance with the invention.
Figure 5:
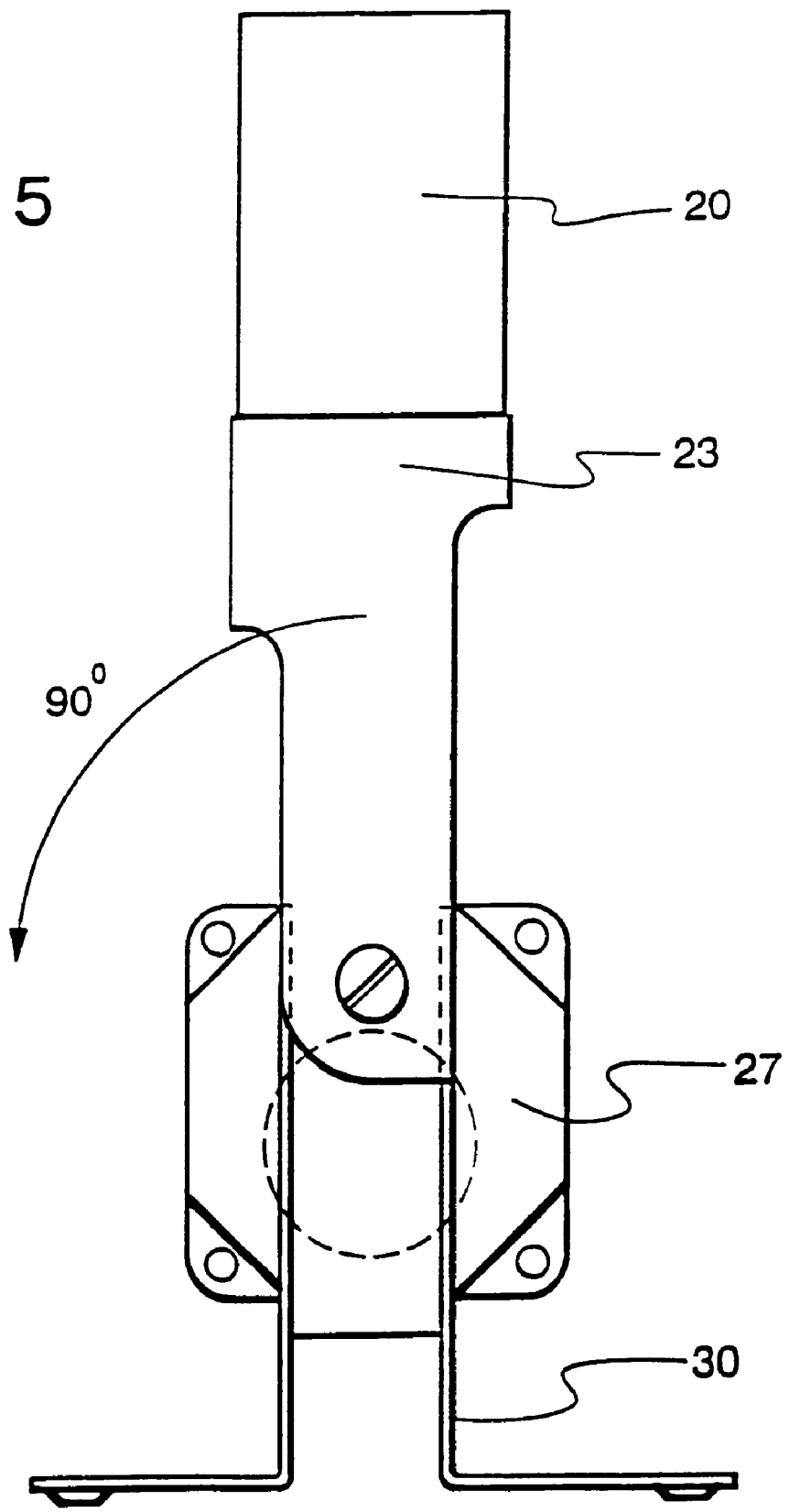
FIG. 5 is a side view of the complete injection device with the flask inserted for use in accordance with the invention.

FIGS. 4 and 5 are front and side views respectively of an injection device 19 for use in accordance with a preferred embodiment of the invention with mold and microwave transparent flask combination 27 inserted therein. The injection device 19 consists of body member 23 and a base 30. A pneumatic or hydraulic press cylinder 20 is supported by body member 23. Press cylinder 20 has a piston rod 21 with a thrust transmitting rod 22. Press cylinder 20 is preferably pneumatic or hydraulic. Thrust transmitting rod 22 is adapted to press cartridge press stamp 8 into injection cartridge 9 which forces one component denture base resin composition 15 into mold chamber 18 of mold 4. Thrust transmitting rod 22 enters the top of cartridge 9 by pressing against cartridge press stamp 8 as shown in FIG. 3.

The bottom of cartridge 9 has a thread which fits into a mouth piece 10 with a safety ring 14 which itself is located in a resin shell 12 as shown in FIG. 3. This assembly of cartridge 9, mouth piece 10, ring 14 and shell 12 is placed in a metal banjo bolt 11. Bolt 11 is connected to and supported by microwave transparent resin flask 13. The microwave transparent resin flask 13 with the assembly on top is placed in the lower part of injection device 19. In order to place the combination of mold 4 and enclosed by flask 1 with the assembly on top into the lower part of the injection device 19, the upper part of injection device 19 is rotated by 90° as shown in FIG. 5. Lock 24 is adapted to arrest the movable upper part of the injection device 19 after it has rotated 90°. The closed flask has a conical shape with the same angle as the press plates 29 and 31 of the injection device. Press plate 29 is fixed in position, and plate 31 is movable in position.

Movable press plate 31 is pressed by a torsion spring 26. Due to the conical shape of the flask and the press plate, the flask is held in place by the downward force on the flask by rod 22. When injection of one component denture base resin composition into mold 4 enclosed by flask 1 is complete, flask 1 is taken out of device 19, after movable press plate 31 is moved from being positioned against the flask 1 by turning the threaded spindle 25 with the handle 28.

The injection device 19 is preferably made of metal components. Injection cartridge 9, cartridge press stamp 8, mouth piece 10, and resin shell 12 are preferably made of plastic, for example polyethylene, polypropylene, or polycarbonate. Injection cartridge 9 is preferably positioned in protective cartridge shell 7 during the injection of one component denture base resin composition into mold 4.

Thus, the press cylinder 20 drives the piston rod 21 with the thrust transmitting rod 22 into injection cartridge 9. One component denture base resin 15 flows through the mouth piece, the resin shell and the injection channels into the cavity of the mold to form the denture base 16, as shown in FIG. 3. The injection process is completed when there is no further movement of cartridge press stamp 8. The injection force is applied on the resin in injection cartridge 9 for less than 30 minutes, preferably from 1 to 20 minutes, most preferably from 5 to 15 minutes. Then the pressure is removed from the resin by moving piston rod 21 back to its initial position. The upper part of the injection device 19 is unloaded and opened.

The injection cartridge with the mouth piece is removed from injection devise 19 and the loose pressure ram 38 is inserted into the resin shell 12 as shown in FIG. 6. Afterwards the repressing device 36 is fixed on top of the metal banjo bolt 11 so that the press stamp which serves also as press indicator shows the marking 33 and 34 as shown in FIG. 6 to indicate that the one component denture base resin being injected remains under a pressure, preferably in an amount of from about 0.5 MPa to about 6 MPa. By maintaining pressure on the one component denture base resin being injected the polymerization shrinkage is significantly reduced. Then the movable press plate 31 is unlocked with a handle screw 28 and the flask with the repressing device on top is removed from the injection device. Next the complete assembly 32 is placed into a microwave oven. The microwave electromagnetic energy applied by the oven has a wavelength of from about 0.3 centimeter to about 30 centimeter (corresponding to 1–100 gigahertz) and is applied for from 1 to 30, preferably 2 to 15, most preferably 3 to 10 minutes. After microwave polymerization the complete assembly 32 is taken out of the microwave oven and cooled down to room temperature. This process can take place in a water bath of approximately 8 to 25° C. Then the prosthesis is removed by separating the halves of the flask from the plaster mold and by carefully breaking the plaster mold.

One component denture base polymerizable compositions in accordance with the invention preferably include from 20% to 90% more preferably 30% to 80%, most preferably 40% to 70% by weight of mono-, di- tri-, or multifunctional (meth)acrylates. One component denture base polymerizable compositions in accordance with the invention preferably include from 0% to 80%, more preferably 0% to 75%, most preferably 0% to 70% organic fillers; from 0% to 85%, more preferably 0.1% to 70%, most preferably 0.2% to 60% silaned inorganic fillers. One component denture base polymerizable compositions in accordance with the invention preferably include up to 15%, more preferably up to 10%, most preferably up to 5% initiators to initiate the polymerization reaction. One component denture base polymerizable compositions in accordance with the invention preferably include pigments, for example metal oxides or organic pigments to give the material the color, and stabilizers for example hydroquinone, hydroquinone monomethyl ether or other sterically hindered phenols (such as Irganox 1010 from Ciba-Geigy) to improve shelf life of the polymerizable composition. Preferably one component denture base polymerizable compositions in accordance with the invention include plasticizers, such as phthalates or phosphates; opacifiers, such as titanium dioxide, aluminum oxide; and/or preservatives, such as copper-8-hydroxyquinoline or tributyltin oxide.

Preferably polymerizable compounds useful in polymerizable compounds for use in compositions in accordance with the invention include mono-, di-, tri- or multifunctional methacrylates and/or acrylates. Exemplary useful acrylic polymerizable compounds for use in compositions in accordance with the invention have a molecular weight of at least 120 and are within the scope of the general structural formula (I):

wherein R is an organic moiety free of any acrylic and (meth)acrylic moiety, $R_1$ is hydrogen, halogen, alkyl, substituted alkyl or cyano group and n is an integer from 1 to 20, and m is an integer from 1 to 1000. Preferably n to from 1 to 6.

In polymerizable compounds within the scope of general formula I, R serves as a hydrocarbyl spacer unit and preferably is alkyl, aromatic, polyether, polyurethane, polyester, glycol, or polyglycol, either unsubstituted or substituted for example with halogen, especially fluorine.

Polymerizable (meth)acrylic compounds useful to provide polymerizable paste compositions in accordance with the invention include monofunctional monomers and multifunctional oligomers and/or monomers having di- or polyfunctional moieties which are capable of addition polymerization. In general, preferred reactive functionalities which serve as active sites for this polymerization are (meth) acrylic. Monofunctional monomers include cyclohexyl methacrylate, benzyl methacrylate, t-butyl methacrylate, n-butyl methacrylate, isobutyl methacrylate, and 2-ethylhexyl methacrylate. Preferred multifunctional monomers and/or oligomers useful as polymerizable (meth) acrylic compounds in one component denture base resins of the invention are including e.g. allyl(meth)acrylate, ethylenglycol di(meth)acrylate, diethyleneglycol di(meth) acrylate, triethyleneglycol di(meth)acrylate, tetraethylenglycol di(meth)acrylate, trimethylpropane tri(meth)acrylate, 1,3-butyleneglycol di(meth)acrylate, 1,4-butanediol di(meth)acrylate, 1,6-hexanediol di(meth)acrylate, 1,12-dodecanediol di(meth)acrylate, pentaerythritol tetra-(meth) acrylate, tripropyleneglycol di(meth)acrylate, ethoxylated bisphenol A di(meth)acrylate, pentaerythritol tri(meth) acrylate, ethoxylated trimethylolpropane tri(meth)acrylate. Furthermore, mixtures of multifunctional monomers and/or oligomers are useful in the practice of the invention.

Polymerizable acrylic compounds such as bis-GMA and the urethane dimethacrylate formed from the reaction of hydroxyethyl acrylate, hydroxypropyl acrylate, and their methacrylate homologs with 2,2,4-trimethylhexyl-1,6-diisocyanate (hereinafter referred to as "urethane dimethacrylate" or "diacrylate") are especially useful, as are polyaddition products of hydroxyalkyl (meth)acrylates, polyesterdiols and/or polyestertriols and aliphatic diisocyanates and/or triisocyanates.

Polymerizable compounds within the scope of general formula I for use in polymerizable compositions of the invention preferably have a molecular weight of from about 120 g/mol to about 50,000 g/mol. Especially preferred are polymerizable compounds within the scope of general formula I having a molecular weight from about 200 g/mol to about 20,000 g/mol, more preferably from about 300 g/mol to about 15,000 g/mol and most preferably from about 400 g/mol to about 10,000 g/mol.

Organic fillers are preferably used in denture base polymerizable compositions in accordance with the invention. Organic fillers are preferably included in compositions in accordance with the invention in amounts of from 0% to 80%, more preferably from 0% to 75%, and most preferably from 0% to 70%. The organic fillers are preferably splinter and/or bead polymers or co-polymers of high molecular weight, such as polymers formed from mono-, di-, tri- or multifunctional methacrylates and/or acrylates. Bead polymers for use as filler is preferably obtained by suspension polymerization. Splinter polymers for use as filler is preferably obtained by grinding (milling) prepolymerized mono, di, tri or mulifunctional (meth)acrylate polymerizable compositions. Organic fillers may be mixed with silaned inorganic fillers. Polymeric fibers are preferably used as fillers alone or in combination with above mentioned organic and/or inorganic fillers. Exemplary fiber fillers include ultra high molecular weight polyethylene fibers, acrylate fibers, polyester fibers, polyacrylonitrile fibers, polyamide fibers and high temperature resistant fibers, such as, aramide and carbon fibers.

Inorganic fillers are preferably used in denture base polymerizable composition in accordance with the invention. Inorganic fillers are preferably included compositions in accordance with the invention in amounts preferably from 0.1% to 85%, more preferably from 0.1% to 70%, and most preferably from 0.2% to 60%. The inorganic fillers are preferably silaned with 3-methacryloyloxypropyltrimethoxy silane by techniques known to the dental industry to achieve a high bond strength between filler and the polymeric matrix formed from the polymerizable composition. Useful inorganic fillers include pyrogenic silicon dioxide, preferably having a surface area: B.E.T. of about 1–400 $m^2/g$ determined according to DIN 66131, fibers of ceramic, glass, aluminum, silicon compounds and ground glass particles with an average particle size of 0.01 μm to 15 μm. The glass particles preferably have a refractive index adapted to (i.e. approximately equal to) the refractive index of the polymerizable composition matrix, to achieve a high transparency of the one component denture base resin for an esthetic appearance. Inorganic fibers are useful for reinforcement.

Preferred initiators for use in one component denture base resins of the invention are adapted to be stored in polymerizable compositions which include a polymerizable compound having a polymerizable acrylic moiety at temperatures of at least 75° C. and at lower temperatures. Preferred initiators for use in one component denture base resins in accordance with the invention are for example benzopinacole, tert.-butylperbenzoate and tert.-butylperisononanoate that are thermally stable at temperatures less than 50° C., but initiate polymerization at temperatures, greater than 100° C. One component polymerizable composition of the invention is adapted to be stored for one or more years at temperatures less than or equal to 23° C. Preferably one component polymerizable compositions of the invention are adapted to be stored for 3 years at 23° C. without substantial polymerization. Preferred initiators for use in polymerizable compositions in accordance with the invention are believed to polarize and decompose in a microwave field. Preferably a microwave source is used to apply microwaves to initiate polymerization of polymerizable compositions of the invention. Preferably the microwave source provides from about 0.01 to about 10 watts/$cm^2$ of microwave radiation having wavelengths of from about 900 to about 2500 MHz. Polymerization of a polymerizable composition including a thermostable initiator in accordance with the invention is initiated by heat and/or microwave energy. Microwave energy is applied to the polymerizable composition while mold by and embedded in a plaster mold. Water, contained in the plaster, is heated by the microwave energy and, is believed to initiate and accelerate polymerization. Polymerizable compositions useful in accordance with the invention preferably include up to 10% initiator, and most preferably include up to 5% initiator.

Polymerizable compositions in accordance with the invention preferably include from 0.01 to 10% stabilizer, most preferably from 0.05% to 5% stabilizer. Preferred stabilizers for use in polymerizable compositions in accordance with the invention include quinones, phenols and aromatic amines. Suitable pigments for use in polymerizable compositions in accordance with the invention include ferric oxides, $TiO_2$, $Al_2O_3$, $ZrO_2$, other metal oxides and organic pigments, e.g. azo compounds and mixture thereof. Preferably pigments are included in composition of the invention in amounts of up to 1%.

In a preferred embodiment of the invention a one component denture base resin of the invention is polymerized with a polymerization shrinkage of less than 4, preferably less than 3 percent by volume. This is significantly less polymerization shrinkage than conventional dentures. Shrinkage is further reduced to less than about 2%, preferably less than 1% by volume by injecting and polymerizing the polymerizable composition under pressure in accordance with the invention into the mold through a channel surrounded by a metal banjo bolt which shields a reservoir of the one component denture base resin from microwaves. The polymerizable composition enclosed in a metal reservoir does not polymerize when microwaves are applied in the microwave oven to activate the initiator to initiate polymerization of the polymerizable composition. The polymerizable composition in the metal reservoir is progressively pressed into the cavity of the mold as the composition in the mold is converted to polymer where the added material polymerizes with the remainder of the polymerizable composition.

Dental prostheses formed in accordance with the invention preferably are a crowns, bridges, artificial teeth or dentures. Preferably compositions in accordance with the invention are polymerized in the mold by microwave energy to form a denture.

In Examples 13, 14, 28 and 29 dentures are prepared in accordance with the invention in a microwave transparent flask enclosing a mold filled with one component denture base resin composition. The composition is cured in a Moulinex microwave oven with 100 watt-hours (Wh) energy. The Moulinex FM A 530 Q microwave oven operates at a voltage of 220/50 Hz; has a power input of 1350 Watt (maximum); has a power output of 800 Watt (maximum) and emits microwave at a frequency of 2.45 GHz. After curing the flask is cooled down to room temperature.

In comparative Examples 1A, 1B and 1C shown in Table 1 specimens of conventional polymethyl methacrylate denture materials are prepared in a metal flask (Example 1A and 1B) and in an microwave transparent plastic flask (Example 1C) according to the manufacturers instructions for use. The flexural strength, modulus of elasticity and bending properties of the products formed in Examples 13, 14, 28, 29, 1A, 1B and 1C are shown in Table 1. These properties have been measured after 48 hours of storage in water at 37° C.

EXAMPLE 1

A denture base paste is formed by mixing 33.30 g of urethane dimethacrylate formed by reaction of hydroxyethyl methacrylate and 2,2,4-trimethylhexamethylene diisocyanate (Plex 6661-0 by Rohm G. m. b. H.), 46.60 g of, poly(urethane dimethacrylate-co-trimethylolpropane trimethacrylate 99.0:1.0) (a suspension polymer), 19.30 g of pyrogenic silica (HDK-H-2000 made by Wacker-Chemie G. m. b. H. Burghausen, Germany), 0.40 g of tert.-Butylperisononanoate (TBPIN), and 0.40 g of benzopinacole.

EXAMPLE 2

A denture base paste is formed by mixing 33.35 g of urethane dimethacrylate oligomer formed by reaction of hydroxypropyl methacrylate and 2,2,4-trimethylhexamethylene diisocyanate, 3.75 g of trimethylolpropane trimethacrylate (TMPTA), 12.50 g of 2-ethylhexylmethacrylate, 25.00 g of pyrogenic silica (HDK-H-2000 by Wacker-Chemie G. m. b. H.), 25.00 g poly(urethane dimethacrylate-co-trimethylolpropane trimethacrylate 99.0:1.0) (a suspension polymer) and 0.40 tert.-Butylperisononanoate (TBPIN).

EXAMPLE 3

A denture base paste is formed by mixing 5.25 g of alkyl triurethane acrylate (Genomer T 930 sold by Rahn A. G. Zurich, Switzerland), 19.05 g of alkyl polyesterdiurethane methacrylate (Genomer D 900 sold by Rahn A. G. Zurich, Switzerland), 31.85 g of a urethane acrylate (Genomer D 500 sold by Rahn A. G. Zurich, Switzerland), 9.50 g of silaned glass. 33.35 g of pyrogenic silica (HDK-H-2000 sold by Wacker-Chemie G. m. b. H.), 0.50 g of tert.-Butylperisononanoate (TBPIN) and 0.50 g of benzopinacole.

EXAMPLE 4

A denture base paste is formed by mixing 6.50 g of alkyl triurethane acrylate (Genomer T 930 sold by Rahn A. G. Zurich, Switzerland), 15.20 g of alkyl polyester triurethane acrylate (Genomer T 1200 sold by Rahn A. G. Zurich, Switzerland), 29.90 g of a urethane acrylate, (Genomer D 500 sold by Rahn A. G. Zurich, Switzerland), 2.00 g of allyl methacrylate, 6.30 g of silaned glass, 12.10 g of urethane acrylate splinter polymer (made by hammering a polymeric film of a silica-filled, urethane dimethacrylate (Plex 6661-0) followed by ball milling to produce a fine powder), 27.00 g of pyrogenic silica (HDK-H-2000 by Wacker-Chemie G. m. b. H.), 0.50 g of benzopinacole and 0.50 g of tert.-Butylperisononanoate (TBPIN).

EXAMPLE 5

A denture base paste is formed by mixing 6.50 g of alkyltriurethane acrylate (Genomer T 930 sold by Rahn A. G. Zurich, Switzerland), 16.70 g alkyl polyester triurethane acrylate (Genomer T 1200 sold by Rahn A. G. Zurich, Switzerland), 30.40 g of urethane acrylate (Genomer D 500 sold by Rahn A. G. Zurich, Switzerland), 6.30 g of silaned glass, 12.10 g of poly (urethane dimethacrylate-co-trimethylolpropane trimethacrylate 99.0:1.0) (suspension polymer), 27.00 g of pyrogenic silica (HDK-H-2000 by Wacker Chemie G. m. b. H., 0.50 g of benzopinacole and 0.50 g of tert.-Butylperisononanoate (TBPIN).

EXAMPLE 6

A denture base paste is formed by mixing 6.50 g of alkyl triurethane acrylate (Genomer T 930 sold by Rahn A. G. Zurich, Switzerland), 16.70 g alkyl polyester triurethane acrylate (Genomer T 1200 sold by Rahn A. G. Zurich, Switzerland), 30.40 g of urethane acrylate, such as, Genomer D 500 (sold by Rahn A. G. Zurich, Switzerland), 6.30 g of silaned glass, 39.10 g of pyrogenic silica (HDK-H-2000 by Wacker Chemie G. m. b. H.), 0.50 g of benzopinacole and 0.50 g of tert.-Butylperisononanoate (TBPIN).

EXAMPLE 7

A denture base paste is formed by mixing 6.50 g of alkyl triurethane acrylate (Genomer T 930 sold by Rahn A. G. Zurich, Switzerland), 16.70 g alkyl polyester triurethane acrylate (Genomer T 1200 sold by Rahn A. G. Zurich, Switzerland), 30.40 g of a urethane acrylate, such as, Genomer D 500 (sold by Rahn A. G. Zurich, Switzerland), 6.30 g of silaned glass, 12.10 g poly (urethane dimethacrylate-co-trimethlolpropane trimethacrylate 99.0:1.0) (suspension polymer), 27.50 g of pyrogenic silica (HDK-H-2000 by Wacker Chemie G. m. b. H.) and 0.50 g of 3,4-dimethyl-3,4-diphenylhexane.

EXAMPLE 8

A denture base paste is formed by mixing 6.50 g of alkyl triurethane acrylate (Genomer T 930 sold by Rahn A. G. Zurich, Switzerland), 16.70 g alkyl polyester triurethane acrylate (Genomer T 1200 sold by Rahn A. G. Zurich, Switzerland), 30.40 g of a urethane acrylate such as, Genomer D 500 (sold by Rahn A. G. Zurich, Switzerland), 6.30 g of silaned glass fiber, 12.10 g of poly (urethane dimethacrylate-co-trimethylolpropane trimethacrylate 99.0:1.0) (suspension polymer), 27.00 g of pyrogenic silica (HDK-H-2000 by Wacker Chemie G. m. b. H.), 0.50 g of benzopinacole and 0.50 g of tert.-Butylperisononanoate (TBPIN).

EXAMPLE 9

A denture base paste is formed by mixing 5.00 g of alkyl triurethane acrylate (Genomer T 930 sold by Rahn A. G. Zurich, Switzerland), 21.30 g alkyl polyester triurethane acrylate (Genomer T 1200 sold by Rahn A. G. Zurich, Switzerland), 26.80 g of a urethane acrylate such as Genomer D 500 (sold by Rahn A. G. Zurich, Switzerland), 9.00 g of silaned glass, 11.50 g of a splinter polymer (made by hammering a polymeric film of a silica-filled, 1,12-Dodecanediol dimethacrylate followed by ball-milling to a fine powder), 25.40 g of pyrogenic silica (HDK-H-2000 made by Wacker Chemie G. m. b. H.), 0.50 g of benzopinacole and 0.50 g of tert.-Butylperisononanoate (TBPIN).

EXAMPLE 10

A denture base paste is formed by mixing 5.40 g of alkyl triurethane acrylate (Genomer T 930 sold by Rahn A. G. Zurich, Switzerland), 9.80 g alkyl polyester triurethane acrylate (Genomer T 1200 sold by Rahn A. G. Zurich, Switzerland), 42.80 g of a urethane acrylate, such as Genomer D 500 (sold by Rahn A. G. Zurich, Switzerland), 10.00 g of silaned glass, 31.00 g of pyrogenic silica (HDK-H-2000 by Wacker-Chemie G. m. b. H.), 0.50 g of benzopinacole and 0.50 g of tert.-Butylperisononanoate (TBPIN).

EXAMPLE 11

A denture base paste is formed by mixing 5.10 g of alkyl triurethane acrylate (Genomer T 930 sold by Rahn A. G. Zurich, Switzerland), 9.30 g alkyl polyester triurethane acrylate (Genomer T 1200 sold by Rahn A. G. Zurich, Switzerland), 40.60 g of urethane acrylate such as, Genomer D 500 (sold by Rahn A. G. Zurich, Switzerland), 11.50 g of poly (urethane dimethacrylate-co-trimethylolprepane trimethacrylate 99.0:1.0) (suspension polymer), 9.50 g of silaned glass, 23.00 g of pyrogenic silica (HDK-H-2000 by Wacker Chemie G. m. b. H.), 0.50 g of benzopinacole and 0.50 g of tert.-Butylperisononanoate (TBPIN).

EXAMPLE 12

A denture base paste is formed by mixing 5.25 g of alkyl triurethane acrylate (Genomer T 930 sold by Rahn A. G. Zurich, Switzerland), 19.05 g alkyl polyester triurethane acrylate (Genomer T 1200 sold by Rahn A. G. Zurich, Switzerland), 31.85 g of a urethane acrylate, such as, Genomer D 500 (sold by Rahn A. G. Zurich, Switzerland), 9.50 g of silaned glass, 33.35 g of pyrogenic silica (HDK-H-2000 by Wacker-Chemie G. m. b. H.), 0.50 g of benzopinacole and 0.50 g of tert.-Butylperisononanoate (TBPIN).

EXAMPLE 13

A one component denture base resin is formed by mixing 40.60 g of urethane dimethacrylate (Plex 6661-0 sold by Roehm G. m. b. H.), 9.65 g of pyrogenic silica (HDK H2000 by Wacker-Chemie G. m. b. H.), 48.25 g of poly (urethane dimethacrylate-co-trimethylolpropane trimethacrylate 99.0:1.0) (suspension polymer), 0.50 g of benzopinacole and 0.50 g of tert-Butylpersononanoate (TBPIN).

EXAMPLE 14

A one component denture base resin is formed by mixing 4.00 g of alkyl polyester triurethane triacrylate (development product 89-102 sold by Rahn A G, Zurich Swiss), 12.90 g alkyl polyester triurethane acrylate (Genomer T 1200 sold by Rahn A G, Zurich, Swiss), 25.80 g of urethane dimethacrylate (Plex 6661-0 by Roehm G. m. b. H.), 5.00 g of pyrogenic silica (HDK H2000 by Wacker-Chemie G. m. b. H.), 50.65 g of poly (urethane dimethacrylate-co-trimethylolpropane trimethacrylate 99.0:1.0) (suspension polymer), 0.50 g of benzopinacole and 0.50 of tert. Butyl-perisononanoate (TBPIN).

The one component denture base resins of Examples 13 and 14 are injected into the microwave transparent flask and cured by microwave energy in the Moulinex microwave oven. Test specimens are prepared for comparison with conventional denture base materials. The specimens formed of the one component denture base resin have the physical properties shown in Table 1.

EXAMPLE 15

A one component denture base resin is formed by mixing 5.95 g alkyl polyester triurethane triacrylate (development product 89-102 sold by Rahn A G, Zurich, Swiss), 25.50 g of alkyl polyester triurethane acrylate (Genomer T 1200 sold by Rahn A G, Zurich, Swiss), 32.20 g of urethane dimethacrylate (Plex 6661-0 by Roehm G. m. b. H.), 34.00 g of pyrogenic silica (Aerosil R 972 by Degussa), 0.75 g of benzopinacole and 0.75 g of tert.-Butylpersononanoate (TBPIN).

EXAMPLE 16

A one component denture base resin is formed by mixing 65.00 g of urethane dimethacrylate (Plex 6661-0 by Roehm G. m. b. H.), 34.00 g of pyrogenic silica (Aerosil R 972 by Degussa) and 0.50 of tert.-Butylpersononanoate (TBPIN).

EXAMPLE 17

A one component denture base resin is formed by mixing 52.70 g of urethane dimethacrylate (Plex 6661-0 by Roehm G. m. b. H.), 27.70 g of pyrogenic silica (HDK H2000 by Wacker-Chemie G. m. b. H.) 18.50 g of poly (urethane dimethacrylate-co-trimethylolpropane trimethacrylate 99.0:1.0) (suspension polymer), and 0.50 g of tert.-Butylpersononanoate (TBPIN).

EXAMPLE 18

A denture base resin is formed by mixing 51.50 g of urethane dimethacrylate (Plex 6661-0 sold by Roehm GmbH), 18.00 g of poly(urethane dimethacrylate-co-trimethylolpropane trimethacrylate 99.0:1.0) (suspension polymer), 24.40 g of pyrogenic silica (HDK H 2000 made by Wacker GmbH), 4.90 g of high modulus polyacrylate fiber (sold by Schwarzwaelder Textil-Werke, Schenkenzell, Germany), and 0.54 g of tert.-Butylperisononanoate (TBPIN).

EXAMPLE 19

A denture base resin is formed by mixing 51.50 g of urethane dimethacrylate (Plex 6661-0 sold by Roehm GmbH), 18,00 g of poly(urethane dimethacrylate-co-trimethylolpropane trimethacrylate 99.0:1.0) (suspension polymer), 19.40 g of pyrogenic silica (HDK H 2000 made by Wacker GmbH), 10.00 g of high modulus polyacrylate fiber (Schwarzwaelder Textil-Werke), and 0.50 g of tert.-Butylperisononanoate (TBPIN).

EXAMPLE 20

A denture base resin is formed by mixing 49.00 g of urethane dimethacrylate (Plex 6661-0 sold by Roehm GmbH), 17.20 g of poly(urethane dimethacrylate-co-trimethylolpropane trimethacrylate 99.0:1.0) (suspension polymer), 23.20 g of pyrogenic silica (HDK H 2000 made by Wacker GmbH), 4.75 g of high modulus polyacrylate fiber (sold by Schwarzwaelder Textil-Werke), 4.75 of glass fiber (sold by Schwarzwaelder Textil-Werke), and 0.50 g of tert.-Butylperisononanoate (TBPIN).

EXAMPLE 21

A denture base resin is formed by mixing 4.00 g of alkyl polyester triurethane triacrylate (development product 89-102 by Rahn A G), 12.00 g alkyl polyester triurethane acrylate (Genomer T 1200 by Rahn A G), 33.00 g of urethane dimethacrylate (Plex 6661-0 sold by Roehm GmbH), 18.00 g of poly(urethane dimethacrylate-co-trimethylolpropane trimethacrylate 99.0:1.0) (suspension polymer), 23.90 g of pyrogenic silica (HDK H 2000 made by Wacker GmbH), 3.00 g of silaned glass, 5.00 g high modulus polyacrylate fiber (sold by Schwarzwaelder Textil-Werke), and 0.50 g of tert.-Butylperisononanoate (TBPIN).

EXAMPLE 22

A denture base resin is formed by mixing 16.00 g of alkyl polyester triurethane triacrylate (Genomer T 1200 sold by Rahn A G), 33.00 g of urethane dimethacrylate (Plex 6661-0 sold by Roehm GmbH), 18.00 g of poly(urethane dimethacrylate-co-trimethylolpropane trimethacrylate 99.0:1.0) (suspension polymer), 23.90 g of pyrogenic silica (HDK H 2000 made by Wacker GmbH), 3.00 g of silaned glass, 5.00 g high modulus polyacrylate fiber (sold by Schwarzwaelder Textil-Werke), and 0.50 g of tert.-Butylperisononanoate (TBPIN).

EXAMPLE 23

A denture base resin is formed by mixing 49.00 g of urethane dimethacrylate (Plex 6661-0 sold by Roehm GmbH), 17.20 g of poly(urethane dimethacrylate-co-trimethylolpropane trimethacrylate 99.0:1.0) (suspension polymer), 23.10 g of pyrogenic silica (HDK H 2000 made by Wacker GmbH), 4.80 g of silaned glass, 4.80 g high modulus polyacrylate fiber (sold by Schwarzwaelder Textil-Werke), and 0.50 g of tert.-Butylperisononanoate (TBPIN).

EXAMPLE 24

A denture base resin is formed by mixing 4.90 g of alkyl polyester triurethane triacrylate (development product 89-102 by Rahn A G), 18.60 g alkyl polyester triurethane acrylate (Genomer T 1200 sold by Rahn A G), 28.40 g of urethane dimethacrylate (Plex 6661-0 sold by Roehm GmbH), 13.70 g of poly(urethane dimethacrylate-co-trimethylolpropane trimethacrylate 99.0:1.0) (suspension polymer), 25.45 g of pyrogenic silica (HDK H 2000 made by Wacker G m b H), 2.95 g of silaned glass, 4.90 g high modulus polyacrylate fiber (sold by Schwarzwaelder Textil-Werke), and 0.49 g of tert.-Butylperisononanoate (TBPIN).

EXAMPLE 25

A denture base resin is formed by mixing 3.90 g of alkyl polyester triurethane triacrylate (development product 89-102 sold by Rahn A G), 18.70 g alkyl polyester triurethane acrylate (Genomer T 1200 by Rahn A G), 28.50 g of urethane dimethacrylate (Plex 6661-0 sold by Roehm GmbH), 15.80 g of poly(urethane dimethacrylate-co-trimethylolpropane trimethacrylate 99.0:1.0) (suspension polymer), 25.60 g of pyrogenic silica (HDK H 2000 made by Wacker GmbH), 3.00 g of silaned glass, 3.50 g high modulus polyacrylate fiber (sold by Schwarzwaelder Textil-Werke), and 0.50 g of tert.-Butylperisononanoate (TBPIN).

EXAMPLE 26

A denture base resin is formed by mixing 3.00 g of alkyl polyester triurethane triacrylate (development product 89-102 sold by Rahn A G), 12.00 g alkyl polyester triurethane acrylate (Genomer T 1200 sold by Rahn A G), 36.00 g of urethane dimethacrylate (Plex 6661-0 sold by Roehm GmbH), 15.00 g of poly(urethane dimethacrylate-co-trimethylolpropane trimethacrylate 99.0:1.0) (suspension polymer), 26.00 g of pyrogenic silica (HDK H 2000 made by Wacker GmbH), 3.00 g of silaned glass, 4.00 g high modulus polyacrylate fiber (Schwarzwaelder Textil-Werke), and 0.50 g of tert.-Butylperisononanoate (TBPIN).

EXAMPLE 27

A denture base resin is formed by mixing 12.05 g of alkyl polyester triurethane triacrylate (development product 89-102 sold by Rahn A G), 37.20 g of urethane dimethacrylate (Plex 6661-0 sold by Roehm GmbH), 18.10 g of poly(urethane dimethacrylate-co-trimethylolpropane trimethacrylate 99.0:1.0) (suspension polymer), 24.50 g of pyrogenic silica (HDK H 2000 made by Wacker GmbH), 3.00 g of silaned glass, 4.00 g high modulus polyacrylate fiber (sold by Schwarzwaelder Textil-Werke), and 0.50 g of tert.-Butylperisononanoate (TBPIN).

EXAMPLE 28

A denture base paste is formed by mixing 2.85 g of alkyl polyester triurethane triacrylate (development product 89-102 sold by Rahn A G), 11.40 g alkyl polyester triurethane acrylate (Genomer T 1200 by Rahn A G), 34.20 g of urethane dimethacrylate (Plex 6661-0 by Roehm GmbH), 19.00 g of poly (urethane dimethacrylate-cotrimethylolpropane trimethacrylate 99.0:1.0) (suspension polymer), 24.70 g of pyrogenic silica (HDK H 2000 by Wacker GmbH), 2.85 g of silaned glass, 3.80 g of high modulus polyacrylate fiber (Schwarzwaelder Textil-Werke), and 0.50 g of tert.-Butylperisononanoate (TBPIN). This paste is injected into a mold within a microwave transparent flask, which is positioned in a microwave oven and exposed to microwaves. The flask is then removed from the oven, opened and a denture is removed from the mold. The specimens formed of the one component denture base resin have the physical properties shown in Table 1.

EXAMPLE 29

A denture base paste is formed by mixing 2.80 g of alkyl polyester triurethane triacrylate (development product 89-102 sold by Rahn A G), 11.40 g alkyl polyester triurethane acrylate (Genomer T 1200 by Rahn A G), 34.00 g of urethane dimethacrylate (Plex 6661-0 by Roehm GmbH), 18.90 g of poly (urethane dimethacrylate-co-trimethylolpropane trimethacrylate 99.0:1.0) (suspension polymer), 24.60 g of pyrogenic silica (HDK H 2000 by Wacker GmbH), 2.85 g of silaned glass, 3.80 g of high modulus polyacrylate fiber (Schwarzwaelder Textil-Werke), 0.50 g of benzopinacole and 0.50 g of tert.-Butylperisononanoate (TBPIN). This paste is injected into a mold within a microwave transparent flask, which is positioned in a microwave oven and exposed to microwaves for 5 minutes. The flask is then removed from the oven, opened and a denture product is removed from the mold. The specimens formed of the one component denture base resin have the physical properties shown on Table 1.

progressively pressing to maintain pressure upon and inject a second portion of said composition from said channel into said mold and polymerizing said second portion of said composition.

2. The method of claim 1 wherein said polymerizable composition further comprises a plasticizer or preservative.

3. The method of claim 1 wherein said flask has a body wall formed from fibre reinforced resin microwave transparent material.

4. The method of claim 1 wherein said composition is polymerized in from one to fifteen minutes.

5. The method of claim 4 wherein said injecting occurs in from one to twenty minutes.

6. A curable system, comprising:

a polymerizable composition positioned within a dental prosthesis mold chamber enclosed by a chamber wall of a mold, said mold being enclosed by a microwave permeable flask having a metal member with a channel, said channel extending through said chamber wall, said flask affixed to a repressing device having a ram and positioned in a microwave oven, a first portion of said composition being polymerized in said mold, said ram progressively pressing and injecting a second portion of said composition from said channel into said mold chamber, and polymerizing said second portion of said composition in said mold chamber.

7. The system of claim 6 wherein said first and said second portion of said composition cure to form an artificial tooth, crown, bridge or denture.

8. The system of claim 6 wherein said composition is cured to form a polymeric product with less than 3 percent change in volume between said polymerizable composition and said polymeric product.

TABLE 1

|  | EXAMPLES | | | | | | |
|---|---|---|---|---|---|---|---|
|  | 13 | 14 | 28 | 29 | 1A | 1B | 1C |
| Product | One Component, denture base resin | | One Component denture base resin | | Selectaplus H | Lucitone | Acron |
| Color | unpigmented, transparent | | Unpigmented, transparent | | Pink | Pink | Pink |
| 1)Flexural Strength [MPa] | 71 ± 6 | 69 ± 2 | 71 ± 5 | 81 ± 5 | 68 ± 5 | 58 ± 5 | 65 ± 6 |
| 1)Modulus of Elasticity [MPa] | 2850 ± 70 | 2220 ± 60 | 3550 ± 170 | 3640 ± 210 | 2250 ± 240 | 1900 ± 170 | 2100 ± 230 |
| Bending [mm] (maximum) | 4.7 ± 0.5 | 8.1 ± 1.3 | 3.8 ± 0.3 | 4.5 ± 0.3 | 8.4 ± 0.2 | 8.1 ± 0.5 | 7.4 ± 1.0 |
| 2)Transverse breaking force [n] | 59 | 58 | 61 | 69 | 58 | 43 | 40 |

1)According to DIN 13907, except using a Specimen thickness of 2.5 mm
2)According to ISO 1567: 1988

It should be understood that while the present invention has been described in considerable detail with respect to certain specific embodiments thereof, it should not be considered limited to such embodiments but may be used in other ways without departure from the spirit of the invention and the scope of the appended claims.

What is claimed is:

1. A method of making a dental prosthesis, comprising:

providing a first portion of a polymerizable composition in a mold of a dental prosthesis enclosed by a flask having a channel and a repressing device having a ram in a microwave oven, polymerizing a first portion of said composition in said mold, 9. The system of claim 6 wherein said composition comprising a polymerizable methacrylate or acrylate Monomer having a molecular weight between 120 and 50,000 g/mol, filler particles, and a microwave activated initiating system, said composition being adapted to effectively remain substantially without polymerization for at least one year at 23° C., and polymerization of said composition is initiated by transmission of microwaves into said composition.

10. The system of claim 1 further comprising indicating said injecting.

11. The system of claim 6 wherein said composition further comprises benzopinicole and/or tert-butylperisononanoate (TBPIN).

12. The system of claim 9 wherein said composition is maintained at least at 0.5 MPa and said Monomer are a blend of (meth)acrylates.

13. A method of making a denture, comprising:

providing a one component denture base resin composition having a pasty consistency, a microwave transparent fiber reinforced resin flask, a microwave oven and a repressing device (36) having a ram (38), said flask having a metal member with a channel, said flask enclosing a mold having a chamber, said repressing device being affixed to said flask to form an assembly in which said composition is maintained under pressure in said channel, positioning said assembly within said oven, microwave curing a first portion of said one component denture base resin in said mold chamber, injecting a second portion of said composition from said channel into said mold chamber and polymerizing said second portion of said composition.

14. The method of claim 13 wherein said channel extends to a cavity of said mold situated in the microwave transparent resin flask.

15. The method of claim 13 further comprising indicating said injecting.

16. A method of making a dental prosthesis, comprising:

providing a one polymerizable composition, injecting said composition into a mold enclosed by a flask, said mold having a chamber wall having the form of the outer surface of said dental prosthesis, and enclosing a mold chamber, said flask having a channel extending through said chamber wall, said flask having a body wall, at least a substantial portion of said body wall being substantially transparent to said microwave energy, affixing a repressing device having a ram to said flask, positioning said flask and repressing device in a microwave oven, polymerizing a first portion of said composition in said mold, progressively pressing and injecting a second portion of said composition from said channel into said mold chamber and polymerizing said second portion of said composition in said mold.

17. The method of claim 1 wherein said prosthesis is a crown, bridge, tooth or denture.

18. The method of claim 1 wherein said polymerizable composition is a one component polymerizable composition having a Monomer and an initiating system adapted to polymerize by applying microwave energy to said composition, and said composition is injected into said mold, said mold has a chamber wall having the form of the outer surface of said dental prosthesis, said flask has a metal member, and said channel extends through said metal member, said flask has a body wall, at least a substantial portion of said body wall is substantially transparent to said microwave energy.

19. The method of claim 13 wherein said ram has markings, and said markings indicate said injection of a second portion of said composition in said channel at from 0.5 MPa to 6 MPa.

20. The method of claim 16 further comprising indicating said injecting.

21. The method of claim 18 wherein said composition comprises at least one initiator, and said composition is adapted to remain substantially free of polymerization when stored for at least one year at 23° C. without applying microwave radiation.

22. The method of claim 1 wherein said composition further comprises a material selected from the group consisting of inorganic filler, organic filler, inorganic fiber, organic fiber, and pigment.

23. The method of claim 1 wherein said composition is polymerized in said mold by microwave energy to form a denture.

24. The method of claim 1 wherein said polymerizable composition is adapted to polymerize to form a polymeric product having a volumetric shrinkage of less than 4%.

25. The method of claim 18 wherein said composition comprises one more Monomers having a molecular weight of at least 400 g/mol.

26. The method of claim 18 wherein said Monomer is selected from the group consisting of mono-functional ester of acrylic, di-functional ester of acrylic, tri-functional ester of acrylic, multi-functional ester of acrylic and methacrylic acid.

27. The method of claim 1 wherein said composition further comprises organic fillers with an average particle size between 0.1 $\mu$m–100 $\mu$m.

28. The method of claim 27 wherein said composition further comprises organic fillers produced by polymerization of a member selected from the group consisting of methacrylic acid, mono-functional ester of acrylic, di-functional ester of acrylic, tri-functional ester of acrylic, and multi-functional ester of acrylic.

29. The method of claim 16 further comprising indicating said injecting of said second portion of said composition.

30. The method of claim 1 wherein said composition further comprises initiators which do not substantially initiate polymerization at temperatures less than 80° C.

31. The method of claim 18 wherein said composition further comprises initiators which do not substantially initiate polymerization at temperatures less than 80° C.

32. The method of claim 18 wherein said composition further comprises a material selected from the group consisting of organic filler, inorganic filler, fiber, initiator, stabilizer and pigment.

33. The method of claim 32 wherein said composition further comprises up to about 5 percent by weight initiators.

34. The method of claim 32 wherein said composition further comprises up to about 5 percent by weight a tetraphenylethanediol as an initiator.

35. The method of claim 32 wherein said composition further comprises up to about 5 percent by weight tert-Butylperisononanoate (TBPIN) as an initiator.

36. The method of claim 18 wherein said composition further comprises stabilizer.

37. The method of claim 36 wherein said stabilizer is a quinone, a sterically hindered phenol, or an aromatic amine.

* * * * *